United States Patent
Finley et al.

(10) Patent No.: US 12,272,080 B2
(45) Date of Patent: Apr. 8, 2025

(54) SYSTEMS AND METHODS FOR ANATOMICAL SEGMENTATION

(71) Applicant: Nuvasive, Inc., San Diego, CA (US)

(72) Inventors: Eric Finley, San Diego, CA (US); Sean O'Connor, San Diego, CA (US)

(73) Assignee: Globus Medical Inc., Audubon, PA (US)

(*) Notice: Subject to any disclaimer, the term of this patent is extended or adjusted under 35 U.S.C. 154(b) by 407 days.

(21) Appl. No.: 17/761,037

(22) PCT Filed: Sep. 27, 2020

(86) PCT No.: PCT/US2020/052974
§ 371 (c)(1),
(2) Date: Mar. 16, 2022

(87) PCT Pub. No.: WO2021/062340
PCT Pub. Date: Apr. 1, 2021

(65) Prior Publication Data
US 2022/0351385 A1 Nov. 3, 2022

Related U.S. Application Data

(60) Provisional application No. 62/907,534, filed on Sep. 27, 2019.

(51) Int. Cl.
| | |
|---|---|
| G06T 7/30 | (2017.01) |
| A61B 90/00 | (2016.01) |
| G06T 7/00 | (2017.01) |
| G06T 7/10 | (2017.01) |
| G06V 10/82 | (2022.01) |
| G06V 10/26 | (2022.01) |
| G06V 10/44 | (2022.01) |

(52) U.S. Cl.
CPC .............. *G06T 7/30* (2017.01); *A61B 90/37* (2016.02); *G06T 7/0012* (2013.01); *G06T 7/10* (2017.01);
(Continued)

(58) Field of Classification Search
CPC .......... G06T 7/30; G06T 7/0012; G06T 7/10; G06T 2200/04; G06T 2200/24;
(Continued)

(56) References Cited

U.S. PATENT DOCUMENTS

| | | | | |
|---|---|---|---|---|
| 11,284,846 B2 * | 3/2022 | Graumann | ........... | A61B 6/5235 |
| 11,348,257 B2 * | 5/2022 | Lang | ...................... | A61B 90/92 |

(Continued)

FOREIGN PATENT DOCUMENTS

| | | | | | |
|---|---|---|---|---|---|
| CN | 103156632 | A | * | 6/2013 | |
| CN | 104346799 | A | * | 2/2015 | ............... A61B 6/03 |
| JP | 2010221015 | A | * | 10/2010 | |

OTHER PUBLICATIONS

PCT International Search Report for PCT Application No. PCT/US2020/052974 mailed Nov. 30, 2020 (4 pages).
(Continued)

*Primary Examiner* — Chan S Park
*Assistant Examiner* — Sebastian-Sy Vuchi Ngo

(57) ABSTRACT

A method includes receiving a three-dimensional image dataset of a surgical site of a patient. The method also includes segmenting one or more anatomical features of the surgical site based on the three-dimensional image dataset. The method also includes receiving a two-dimensional image of the surgical site of the patient and registering the two-dimensional image to an image from the three-dimensional image dataset. The method also includes displaying a two-dimensional representation of the segmented one or more anatomical features based on the registered two-dimensional image and the image from the three-dimensional image dataset.

8 Claims, 8 Drawing Sheets

(52) U.S. Cl.
CPC .......... *G06V 10/82* (2022.01); *G06T 2200/04* (2013.01); *G06T 2200/24* (2013.01); *G06T 2207/10081* (2013.01); *G06T 2207/10124* (2013.01); *G06T 2207/20212* (2013.01); *G06T 2207/30012* (2013.01); *G06V 10/267* (2022.01); *G06V 10/454* (2022.01)

(58) Field of Classification Search
CPC . G06T 2207/10081; G06T 2207/10124; G06T 2207/20212; G06T 2207/30012; G06V 10/82; A61B 90/37
See application file for complete search history.

(56) References Cited

U.S. PATENT DOCUMENTS

| | | |
|---|---|---|
| 2017/0112575 A1 | 4/2017 | Li et al. |
| 2017/0178349 A1 | 6/2017 | Ketcha et al. |
| 2021/0186647 A1* | 6/2021 | Elimelech ............ A61B 90/361 |
| 2021/0330250 A1* | 10/2021 | Redmond .............. A61B 90/06 |
| 2023/0177748 A1* | 6/2023 | Aubert ...................... G06T 7/10 382/132 |

OTHER PUBLICATIONS

PCT Written Opinion for PCT Application No. PCT/US2020/052974 mailed Nov. 30, 2020 (7 pages).

Esfandiari et al., "A comparative analysis of intensity-based 2D-3D registration for intraoperative use in pedicle screw insertion surgeries," Int'l Journal of Computer Assisted Radiology and Surgery, 2019, 14:1725-1739.

Newell et al., "An intraoperative fluoroscopic method to accurately measure the post-implantation position of pedicle screw," Int'l Journal of Computer Assisted Radiology and Surgery, 2018, 13:1257-1267.

Penney et al., "Deforming a Preoperative Volume to Represent the Intraoperative Scene," Computer Aided Surgery, 2002, 7(2):63-73.

* cited by examiner

SYSTEMS AND METHODS FOR ANATOMICAL SEGMENTATION

CROSS REFERENCE

This application is a National Stage Application of PCT/US2020/052974, filed Sep. 27, 2020, which claims priority to U.S. Provisional Application No. 62/907,534, filed on Sep. 27, 2019, the entire disclosures of which are incorporated herein by reference in their entirety.

FIELD

This disclosure relates intraoperative imaging during a surgical procedure.

BACKGROUND

Surgeries which involve passing surgical instruments near or through tissues or areas having neural structures which, if contacted, may result in neurological deficit for the patient are common. For example, spine surgery may be employed to address any number of different spinal disorders. During spine surgery, it is necessary to create an operative corridor extending between an incision site and the spinal column. Depending on the approach or trajectory to the spine (e.g., anterior, posterior, lateral, etc.), different tissues will need to be traversed in order to establish the operative corridor. Further, if a patient's spinal column is manipulated during surgery, soft tissues surrounding the vertebra may be impacted. Regardless of the approach or trajectory, it is helpful to incorporate the use of intraoperative imaging to assist one or more medical professionals with one or more procedures corresponding to a surgical site.

SUMMARY

In one embodiment, a method comprises receiving a three-dimensional image dataset of a surgical site of a patient. The method also comprises segmenting one or more anatomical features of the surgical site based on the three-dimensional image dataset. The method also comprises receiving a two-dimensional image of the surgical site of the patient and registering the two-dimensional image to an image from the three-dimensional image dataset. The method also comprises displaying a two-dimensional representation of the segmented one or more anatomical features based on the registered two-dimensional image and the image from the three-dimensional image dataset.

In another embodiment, a method comprises receiving a three-dimensional image dataset of a surgical site of a patient. The method also comprises segmenting one or more anatomical features of the surgical site based on the three-dimensional image dataset, wherein segmenting includes identifying one or more vertebrae and separating the identified one or more vertebrae from the three-dimensional image dataset. The method also comprises receiving a two-dimensional image of the surgical site of the patient and registering the two-dimensional image to an image from the three-dimensional image dataset. The method also comprises displaying a two-dimensional representation of the segmented one or more anatomical features based on the registered two-dimensional image and the image from the three-dimensional image dataset.

In another embodiment, a method comprises receiving a three-dimensional image dataset of a surgical site of a patient. The method also comprises segmenting one or more anatomical features of the surgical site based on the three-dimensional image dataset, wherein segmenting includes identifying one or more vertebrae and separating the identified one or more vertebrae from the three-dimensional image dataset. The method also comprises generating one or more three-dimensional image datasets corresponding to the separated identified one or more vertebrae and combining two or more three-dimensional image datasets from the generated one or more three-dimensional image datasets. The method also comprises receiving a two-dimensional image of the surgical site of the patient and registering the two-dimensional image to an image from the combined two or more three-dimensional image datasets. The method also comprises displaying a two-dimensional representation of the segmented one or more anatomical features based on the registered two-dimensional image and the image from the three-dimensional image dataset.

DETAILED DESCRIPTION

Figure 1:
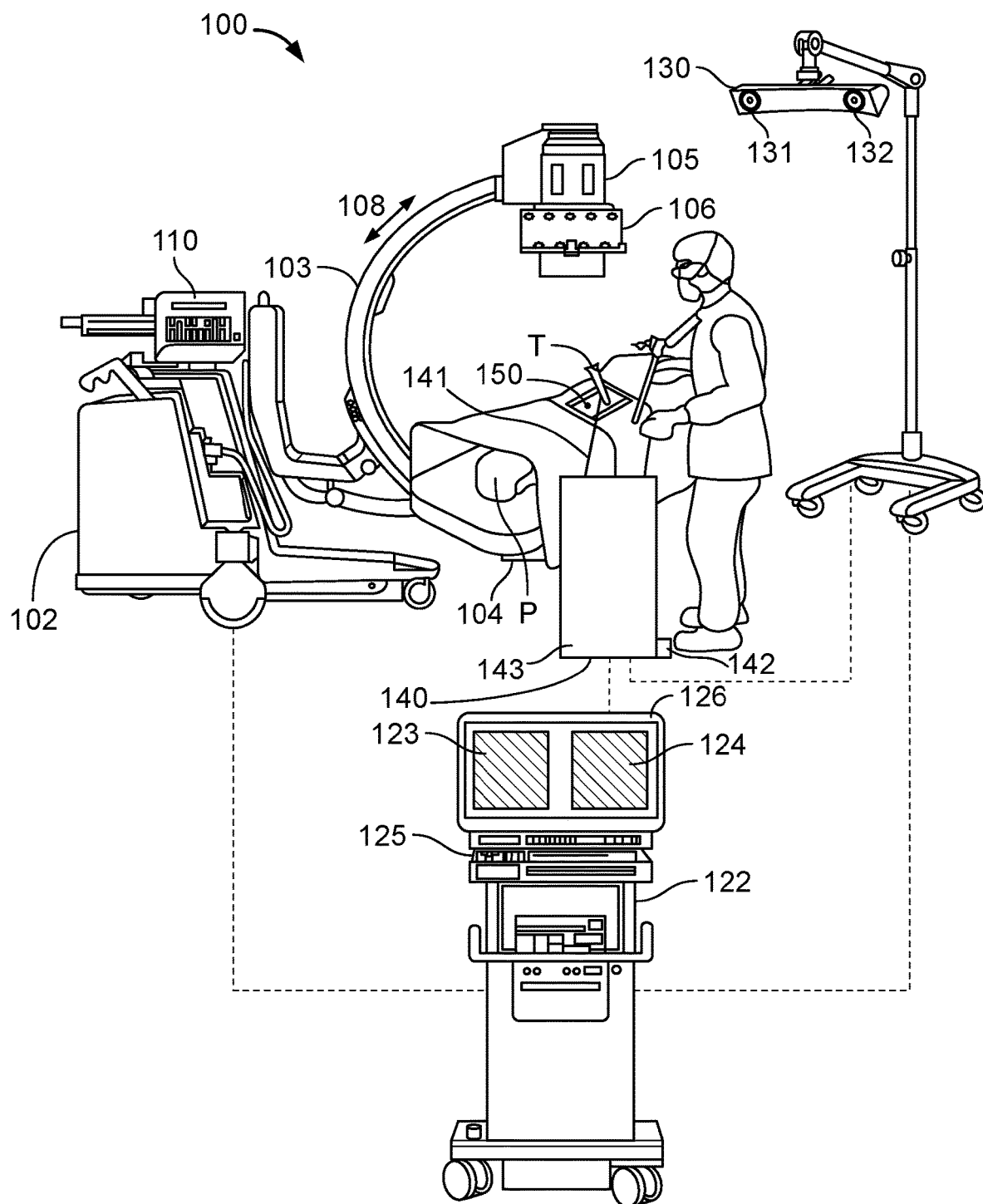
FIG. 1 is a diagram of an example system for performing a surgical procedure, according to an embodiment of the present disclosure.

Illustrative embodiments of the invention are described below. In the interest of clarity, not all features of an actual implementation are described in this specification. It will of course be appreciated that in the development of any such actual embodiment, numerous implementation-specific decisions must be made to active the developers' specific goals, such as compliance with system-related and business-related constraints, which will vary from one implementation to another. Moreover, it will be appreciated that such a development effort might be complex and time-consuming, but nevertheless be a routine undertaking for those of ordinary skill in the art having the benefit of this disclosure. It is furthermore to be readily understood that, although discussed below primarily within the context of spinal surgery, the systems and methods of the present invention may be employed in any number of anatomical settings to provide access to any number of different surgical target sites throughout the body.

In one example, a robotic device is positioned within an operating room that enables the robotic device to access the spine of a patient using one or more approaches while the patient is in a lateral decubitus position throughout a surgical procedure. The one or more approaches may include, for example, a direct lateral approach, an anterior approach, an antero-lateral approach and a posterior approach to the spine of the patient. Continuing with this example, a tracking device is configured to capture the position of the patient based on one or more registration pins and arrays attached to the patient. The tracking device is also configured to capture the position of the robotic device based on one or more tracking arrays coupled to the robotic device. The tracking device is configured to provide the captured position information to a processing device. The processing device is configured to determine a placement of the robotic device based on the required one or more approaches to the spine of the patient and the determined position of the patient relative to the position of the robotic device.

In one scenario, the processing device may display information to assist a user for placing the robotic device in a position relative to the patient that allows for the robotic device to access the spine of the patient according to the one or more approaches associated with a given surgical procedure. For example, the processing device may determine that the robotic device needs to be moved along one or more axes prior to beginning the surgical procedure. In this example, a user may view a display associated with the processing device and follow a virtual path in order to place the robotic device in the required position.

In one example, the robotic device is coupled to a lift device that allows for the robotic device to be raised or lowered depending on a given surgical procedure. In one example, the lift device includes a hydraulic actuator. In another example, the lift device includes an electric actuator. In one example, the lift device includes at least one position sensor configured to determine the vertical position of the lift device. In one scenario, once the vertical position of the robotic device is set, the robotic device is configured to remain at that vertical position during the duration of the surgical procedure.

Referring now to the figures, FIG. 1 is a diagram of an example system 100 for performing a surgical procedure. The example system 100 includes a base unit 102 supporting a C-Arm imaging device 103. The C-Arm 103 includes a radiation source 104 that is positioned beneath the patient P and that directs a radiation beam upward to the receiver 105. The receiver 105 of the C-Arm 103 transmits image data to a processing device 122. The processing device 122 may communicate with a tracking device 130 to obtain position and orientation information of various instruments (e.g., instrument T) used during the surgical procedure. The tracking device 130 may communicate with a robotic device 140 to provide location information of various tracking elements, such as marker 150. The robotic device 140 and the processing device 122 may communicate via one or more communication channels.

The base unit 102 includes a control panel 110 through which a user can control the location of the C-Arm 103, as well as the radiation exposure. The control panel 110 thus permits the radiology technician to "shoot a picture" of the surgical site at a surgeon's direction, control the radiation dose, and initiate a radiation pulse image.

The C-Arm 103 may be rotated about the patient P in the direction of the arrow 108 for different viewing angles of the surgical site. In some instances, implants or instrument T may be situated at the surgical site, necessitating a change in viewing angle for an unobstructed view of the site. Thus, the position of the receiver relative to the patient P, and more particularly relative to the surgical site of interest, may change during a procedure as needed by the surgeon or radiologist. Consequently, the receiver 105 may include a tracking target 106 mounted thereto that allows tracking of the position of the C-Arm 103 using the tracking device 130. By way of example only, the tracking target 106 may include a plurality of infrared (IR) reflectors or emitters spaced around the target, while the tracking device 130 is configured to triangulate the position of the receiver 105 from the IR signals reflected or emitted by the tracking target 106.

The processing device 122 can include a digital memory associated therewith and a processor for executing digital and software instructions. The processing device 122 may also incorporate a frame grabber that uses frame grabber technology to create a digital image for projection as displays 123 and 124 on a display device 126. The displays 123 and 124 are positioned for interactive viewing by the surgeon during the procedure. The two displays 123 and 124 may be used to show images from two views, such as lateral and A/P, or may show a baseline scan and a current scan of the surgical site, or a current scan and a "merged" scan based on a prior baseline scan and a low radiation current scan. An input device 125, such as a keyboard or a touch screen, can allow the surgeon to select and manipulate the on-screen images. It is understood that the input device may incorporate an array of keys or touch screen icons corresponding to the various tasks and features implemented by the processing device 122. The processing device 122 includes a processor that converts the image data obtained from the receiver 105 into a digital format. In some cases, the C-Arm 103 may be operating in the cinematic exposure mode and generating many images each second. In these cases, multiple images can be averaged together over a short time period into a single image to reduce motion artifacts and noise.

The tracking device 130 includes sensors 131 and 132 for determining location data associated with a variety of elements (e.g., an infrared reflector or emitter) used in a surgical procedure. In one example, the sensors 131 and 132 may be a charge-coupled device (CCD) image sensor. In another example, the sensors 131 and 132 may be a complementary metal-oxide-semiconductor (CMOS) image sensor. It is also envisioned that a different number of other image sensors may be used to achieve the functionality described.

In one aspect, the robotic device 140 may assist with holding an instrument T relative to the patient P during a surgical procedure. In one scenario, the robotic device 140 may be configured to maintain the instrument T in a relative position to the patient P as the patient P moves (e.g., due to breathing) or is moved (e.g., due to manipulation of the patient's body) during the surgical procedure.

The robotic device 140 may include a robot arm 141, a pedal 142, and a mobile housing 143. The robotic device 140 may also be in communication with a display such as display 126. The robotic device 140 may also include a fixation device to fix the robotic device 140 to an operating table.

The robot arm 141 may be configured to receive one or more end effectors depending on the surgical procedure and the number of associated joints. In one example, the robot arm 141 may be a six joint arm. In this example, each joint includes an encoder which measures its angular value. The movement data provided by the one or more encoders, combined with the known geometry of the six joints, may allow for the determination of the position of the robot arm 141 and the position of the instrument T coupled to the robot arm 141. It also envisioned that a different number of joints may be used to achieve the functionality described herein.

The mobile housing 143 ensures easy handling of the robotic device 140 through the use of wheels or handles or both. In one embodiment, the mobile housing 143 may include immobilization pads or an equivalent device. The mobile housing 143 may also include a control unit which provides one or more commands to the robot arm 141 and allows a surgeon to manually input data through the use of an interface, such as a touch screen, a mouse, a joystick, a keyboard or similar device.

In one example, the processing device 122 is configured to capture a pose of an instrument T via the tracking device 130. The captured pose of the instrument includes a combination of position information and orientation information. In this example, the pose of the instrument T is based on a user defined placement at a surgical site of the patient P. The user defined placement is based on movement of the instrument T by a surgeon or the robotic device 140 or both. In one scenario, the instrument comprises one or more infrared reflectors or emitters. Continuing with this example, the processing device 122 is configured to determine a range of movement of the instrument T corresponding to the captured pose of the instrument T. The range of movement is associated with the actuation of one or more components (e.g., one or more links and joints) of the robotic device 140. The processing device 122 is configured to determine one or more instructions for actuating the one or more components of the robotic device 140 according to the determined range of movement. Further, the processing device 122 is configured to provide the one or more instructions to the robotic device 140.

In another example, in response to the captured pose of the instrument T, the processing device 122 is configured to determine an axis for pivoting the instrument T and a range of degrees within one or more planes for pivoting the instrument T about the determined axis. In this example, the processing device 122 is configured to provide the one or more instructions to limit a movement to robotic device 140 for pivoting the instrument T coupled to the robotic device 140. The robotic device 140, as described herein, is configured to convert the one or more instructions for enabling the instrument T to be pivoted according to the determined axis and the range of degrees within one or more planes.

Figure 2:
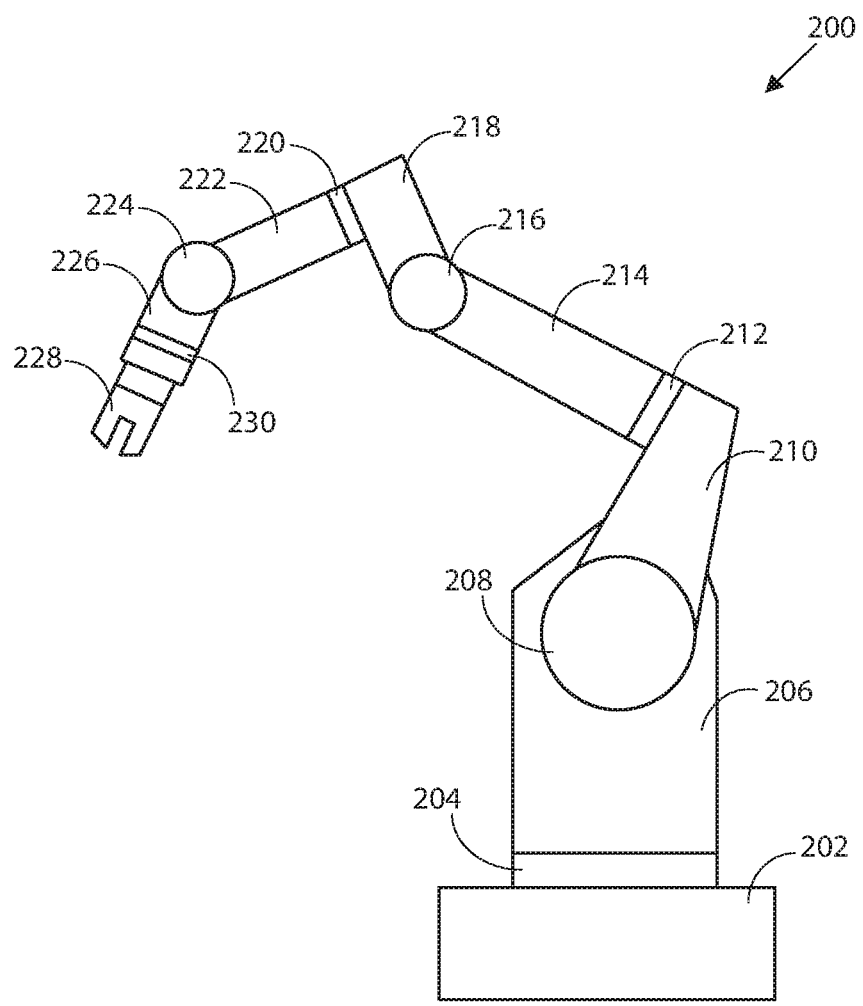
FIG. 2 depicts an example robotic device that may be used during a surgical procedure, according to an embodiment of the present disclosure.

FIG. 2 illustrates an example robotic device 200 that may be used during a surgical procedure. The robotic device 200 may contain hardware, such as a processor, memory or storage, and sensors that enable the robotic device 200 for use in a surgical procedure. The robotic device 200 may be powered by various means such as electric motor, pneumatic motors, hydraulic motors, etc. The robotic device 200 includes a base 202, links 206, 210, 214, 218, 222, and 226, joints 204, 208, 212, 216, 220, 224, and 230, and manipulator 228.

The base 202 may provide a platform in order to provide support for the robotic device 200. The base 202 may be stationary or coupled to wheels in order to provide movement of the robotic device 200. The base 202 may comprise any number of materials such as aluminum, steel, stainless steel, etc., that may be suitable for a given environment associated with the robotic device 200.

The links 206, 210, 214, 218, 222, and 226 may be configured to be moved according to a programmable set of instructions. For instance, the links may be configured to follow a predetermined set of movements (e.g., a limited range of movements based on a captured pose of an instrument) in order to accomplish a task under the supervision of a user. By way of example, the links 206, 210, 214, 218, 222, and 226 may form a kinematic chain that defines relative movement of a given link of links 206, 210, 214, 218, 222, and 226 at a given joint of the joints 204, 208, 212, 216, 220, 224, and 230.

The joints 204, 208, 212, 216, 220, 224, and 230 may be configured to rotate through the use of a mechanical gear system. In one example, the mechanical gear system is driven by a strain wave gearing, a cycloid drive, etc. The mechanical gear system selected would depend on a number of factors related to the operation of the robotic device 200 such as the length of the given link of the links 206, 210, 214, 218, 222, and 226, speed of rotation, desired gear reduction, etc. Providing power to the joints 204, 208, 212, 216, 220, 224, and 230 will allow for the links 206, 210, 214, 218, 222, and 226 to be moved in a way that allows the manipulator 228 to interact with an environment.

In one example, the manipulator 228 is configured to allow the robotic device 200 to interact with the environment according to one or more constraints. In one example, the manipulator 228 performs appropriate placement of an element through various operations such as gripping a surgical instrument. By way of example, the manipulator 228 may be exchanged for another end effector that would provide the robotic device 200 with different functionality.

In one example, the robotic device 200 is configured to operate according to a robot operating system (e.g., an operating system designed for specific functions of the robot). A robot operating system may provide libraries and tools (e.g., hardware abstraction, device drivers, visualizers, message-passing, package management, etc.) to enable robot applications.

Figure 3:
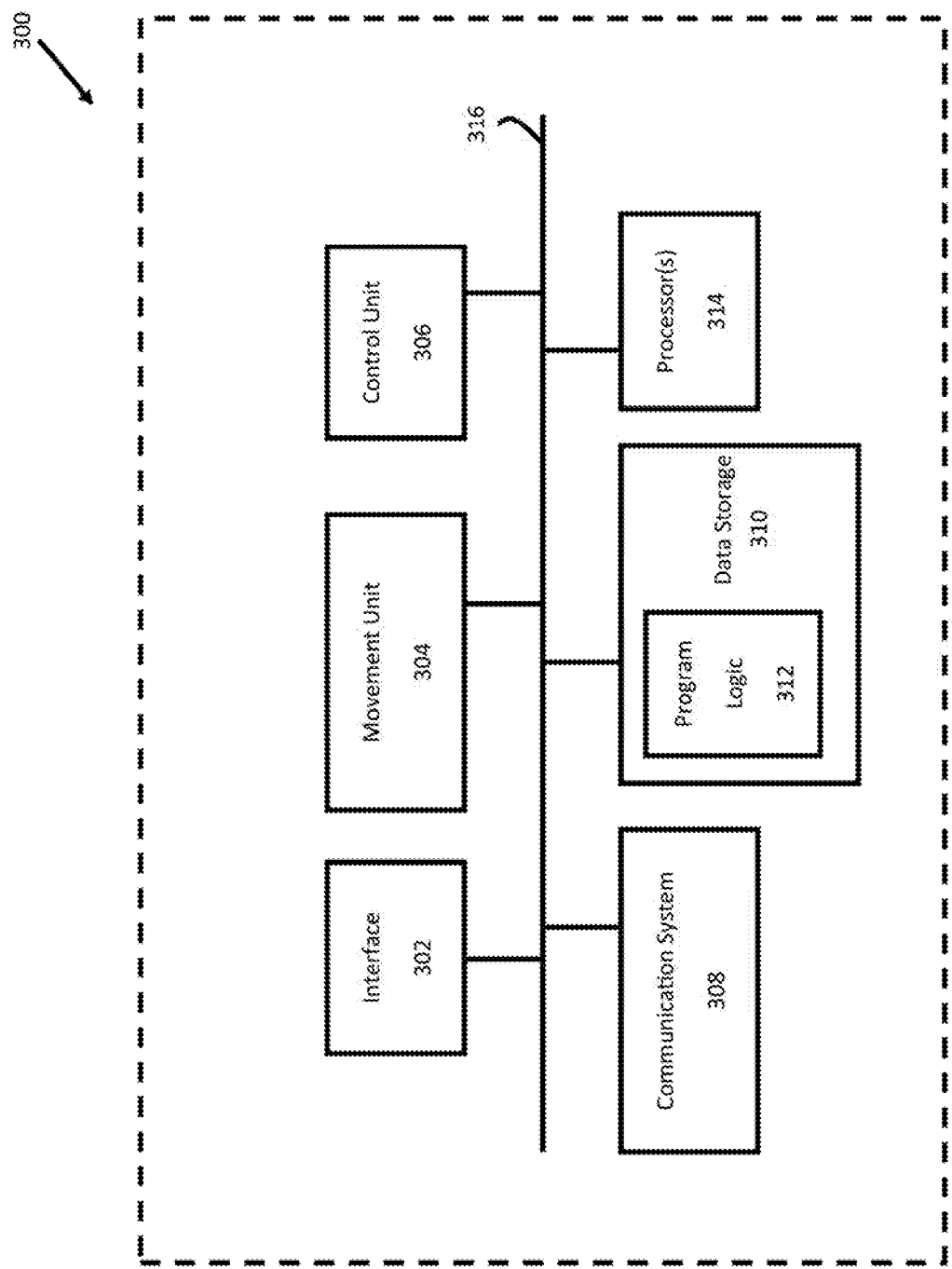
FIG. 3 depicts a block diagram of a computing device, according to an embodiment of the present disclosure.

FIG. 3 is a block diagram of a computing device 300, according to an example embodiment. In some examples, some components illustrated in FIG. 3 may be distributed across multiple computing devices (e.g., desktop computers, servers, hand-held devices, etc.). However, for the sake of the example, the components are shown and described as part of one example device. The computing device 300 may include an interface 302, a movement unit 304, a control unit 306, a communication system 308, a data storage 310, and a processor 314. Components illustrated in FIG. 3 may be linked together by a communication link 316. In some examples, the computing device 300 may include hardware to enable communication within the computing device 300 and another computing device (not shown). In one embodiment, the robotic device 140 or the robotic device 200 may include the computing device 300.

The interface 302 may be configured to allow the computing device 300 to communicate with another computing device (not shown). Thus, the interface 302 may be configured to receive input data from one or more devices. In some examples, the interface 302 may also maintain and manage records of data received and sent by the computing device 300. In other examples, records of data may be maintained and managed by other components of the computing device 300. The interface 302 may also include a receiver and transmitter to receive and send data. In some examples, the interface 302 may also include a user-interface, such as a keyboard, microphone, touch screen, etc., to receive inputs as well. Further, in some examples, the interface 302 may also interface with output devices such as a display, speaker, etc.

In one example, the interface 302 may receive an input indicative of location information corresponding to one or more elements of an environment in which a robotic device (e.g., robotic device 140, robotic device 200) resides. In this example, the environment may be an operating room in a hospital comprising a robotic device configured to function during a surgical procedure. The interface 302 may also be configured to receive information associated with the robotic device. For instance, the information associated with the robotic device may include operational characteristics of the robotic device and a range of motion with one or more components (e.g., joints 204, 208, 212, 216, 220, 224, and 230) of the robotic device (e.g., robotic device 140, robotic device 200).

The control unit 306 of the computing device 300 may be configured to run control software which exchanges data with components (e.g., robot arm 141, robot pedal 142, joints 204, 208, 212, 216, 220, 224, and 230, manipulator 228, etc.) of a robotic device (e.g., robotic device 140, robotic device 200) and one or more other devices (e.g., processing device 122, tracking device 130, etc.). The control software may communicate with a user through a user interface and display monitor (e.g., display 126) in communication with the robotic device. The control software may also communicate with the tracking device 130 and the processing device 122 through a wired communication interface (e.g., parallel port, USB, etc.) and/or a wireless communication interface (e.g., antenna, transceivers, etc.). The control software may communicate with one or more sensors to measure the efforts exerted by the user at the instrument T mounted to a robot arm (e.g., robot arm 141, link 226). The control software may communicate with the robot arm to control the position of the robot arm relative to the marker 150.

As described above, the control software may be in communication with the tracking device 130. In one scenario, the tracking device 130 may be configured to track the marker 150 that is attached to the patient P. By way of example, the marker 150 may be attached to a spinous process of a vertebra of the patient P. In this example, the marker 150 may include one or more infrared reflectors that are visible to the tracking device 130 to determine the location of the marker 150. In another example, multiple markers may be attached to one or more vertebrae and used to determine the location of the instrument T.

In one example, the tracking device 130 may provide updates in near real-time of the location information of the marker 150 to the control software of the robotic device 140. The robotic device 140 may be configured to receive updates to the location information of the marker 150 from the tracking device 130 via a wired and/or wireless interface. Based on the received updates to the location information of the marker 150, the robotic device 140 may be configured to determine one or more adjustments to a first position of the instrument T in order to maintain a desired position of the instrument T relative to the patient P.

In one embodiment, the control software may include independent modules. In an exemplary embodiment, these independent modules run simultaneously under a real time environment and use a shared memory to ensure management of the various tasks of the control software. The modules may have different priorities, such as a safety module having the highest priority, for example. The safety module may monitor the status of the robotic device 140. In one scenario, the safety module may send an instruction to the control unit 306 to stop the robot arm 141 when a critical situation is detected, such as an emergency stop, software failure, or collision with an obstacle, for example.

In one example, the interface 302 is configured to allow the robotic device 140 to communicate with other devices (e.g., processing device 122, tracking device 130). Thus, the interface 302 is configured to receive input data from one or more devices. In some examples, the interface 302 may also maintain and manage records of data received and sent by other devices. In other examples, the interface 302 may use a receiver and transmitter to receive and send data.

The interface 302 may be configured to manage the communication between a user and control software through a user interface and display screen (e.g., via displays 123 and 124). The display screen may display a graphical interface that guides the user through the different modes associated with the robotic device 140. The user interface may enable the user to control movement of the robot arm 141 associated with the beginning of a surgical procedure, activate a given mode to be used during a surgical procedure, and stop the robot arm 141 if needed, for example.

The movement unit 304 may be configured to determine the movement associated with one or more components of the robot arm 141 to perform a given procedure. In one embodiment, the movement unit 304 may be configured to determine the trajectory of the robot arm 141 using forward and inverse kinematics. In one scenario, the movement unit 304 may access one or more software libraries to determine the trajectory of the robot arm 141. In another example, the movement unit 304 is configured to receive one or more instructions for actuating the one or more components of the robotic device 140 from the processing device 122 according to a determined range of movement of a surgical tool at a surgical site.

The movement unit 304 may include a force module to monitor the forces and torques measured by one or more sensors coupled to the robot arm 141. In one scenario, the force module may be able to detect a collision with an obstacle and alert the safety module.

The control unit 306 may be configured to manage the functions associated with various components (e.g., robot arm 141, pedal 142, etc.) of the robotic device 140. For example, the control unit 306 may send one or more commands to maintain a desired position of the robot arm 141 relative to the marker 150. The control unit 306 may be configured to receive movement data from a movement unit 304.

In one scenario, the control unit 306 can instruct the robot arm 141 to function according to a cooperative mode. In the cooperative mode, a user is able to move the robot arm 141 manually by holding the tool T coupled to the robot arm 141 and moving the instrument T to a desired position. In one example, the robotic device 140 may include one or more force sensors coupled to an end effector of the robot arm 141. By way of example, when the user grabs the instrument T and begins to move it in a direction, the control unit 306 receives efforts measured by the force sensor and combines them with the position of the robot arm 141 to generate the movement desired by the user.

In one scenario, the control unit 306 can instruct the robot arm 141 to function according to a given mode that will cause the robotic device 140 to maintain a relative position of the instrument T to a given IR reflector or emitters (e.g., the marker 150). In one example, the robotic device 140 may receive updated position information of the marker 150 from the tracking device 130 and adjust as necessary. In this example, the movement unit 304 may determine, based on the received updated position information of the marker 150, which joint(s) of the robot arm 141 need to move in order to maintain the relative position of the instrument T with the marker 150.

In another scenario, a restrictive cooperative mode may be defined by a user to restrict movements of the robotic device 140. For the example, the control unit 306 may restrict movements of the robot arm 141 to a plane or an axis, according to user preference. In another example, the robotic device 140 may receive information pertaining to one or more predetermined boundaries within the surgical site that should not intersect with a surgical tool or implant based on a user guided movement of the robot arm 141.

In one embodiment, the robotic device 140 may be in communication with the processing device 122. In one example, the robotic device 140 may provide the position and orientation data of the instrument T to the processing device 122. In this example, the processing device 122 may be configured to store the position and orientation data of the instrument T for further processing. In one scenario, the image processing device 122 may use the received position and orientation data of the instrument T to overlay a virtual representation of the instrument T on display 126.

In one embodiment, a sensor configured to detect a pressure or force may be coupled to the last joint of the robot arm (e.g., link 226). Based on a given movement of the robot arm, the sensor may provide a reading of the pressure exerted on the last joint of the robot arm to a computing device (e.g., a control unit of the robotic device). In one example, the robotic device may be configured to communicate the force or pressure data to a computing device (e.g., processing device 122). In another embodiment, the sensor may be coupled to an instrument such as a retractor. In this embodiment, the force or pressure exerted on the retractor and detected by the sensor may be provided to the robotic device (e.g., robotic device 140, robotic device 200) or a computing device (e.g., processing device 122) or both for further analysis.

In one scenario, the robotic device may access movement data stored in a memory of the robotic device to retrace a movement along a determined motion path. In one example, the robotic device may be configured to move the surgical tool along the determined motion path to reach or move away from the surgical site.

In another scenario, once the instrument coupled to a robot arm (e.g., robot arm 141, links 206, 210, 214, 218, 222, and 226) of a robotic device reaches a desired pedicle screw trajectory, the robotic device may be configured to receive an input from the surgeon to travel along the desired pedicle screw trajectory. In one example, the surgeon may provide an input to the robotic device (e.g., depressing the pedal 142) to confirm the surgeon's decision to enable the robotic device to travel along the desired pedicle screw trajectory. In another example, a user may provide another form of input to either the robotic device or the computing device to assist with movement of an instrument along a determined motion path.

In one scenario, once the robotic device has received confirmation to travel along the desired pedicle screw trajectory, the robotic device may receive instructions from the movement unit 304 to pivot from the current trajectory to the desired pedicle screw trajectory. The movement unit 304 may provide the control unit 306 the required movement data to enable the robotic device to move along the desired pedicle screw trajectory.

In another aspect, a robotic device (e.g., robotic device 140, robotic device 200) may be configured to pivot about an area of significance based on the captured pose of a surgical tool (e.g., instrument T). For example, the robotic device may be configured to pivot a retractor about the tip of the retractor so that all the steps associated with retraction of soft tissue do not need to be repeated. In one example, the movement unit 304 may determine the trajectory required to pivot the retractor.

In one example, the robotic device may be coupled to a retractor that is holding soft tissue away from a surgical site. In this example, a surgeon may need to slightly reposition the retractor due to a patient movement. To do so, the surgeon may activate a mode on the robotic device that causes the retractor to pivot by moving the robot arm (e.g., robot arm 141, links 206, 210, 214, 218, 222, and 226) according to a trajectory determined by the movement unit 304. In one example, a user may input the direction and amount of movement desired via a computing device (e.g., the processing device 122, computing device 300). After the direction and amount of movement have been entered, the user (e.g., a surgeon) may interface with the robotic device (e.g., depress the pedal 142) to begin the movement of the instrument coupled to the robot arm. In one example, the robotic device may allow a user to view a different aspect of the anatomy without disengaging from a docking point.

In another example, the movement unit 304 may provide one or more trajectories for moving the surgical tool (e.g., instrument T) based on the captured pose of the surgical tool to a computing device (e.g., processing device 122) for display on display 126. In this example, a user may choose from one or more limited movements associated with a given step of a surgical procedure. For example, the one or more limited movements may be associated with a specific direction and amount of movement to be performed through the use of one or more buttons coupled to the robotic device 140 and by an individual applying a force to a portion of the robotic device 140.

In one scenario, the robot arm of the robotic device may be coupled to an instrument such as a dilator. In this scenario, the robotic device may receive one or more commands to pivot about the distal end of the dilator by a predetermined amount of degrees. The movement unit 304 may be configured to determine the trajectory necessary to perform the pivot and provide the determined trajectory information to the control unit 306 for moving the robotic device.

In another aspect, one or more infrared (IR) reflectors or emitters may be coupled to a robot arm (e.g., robot arm 141, links 206, 210, 214, 218, 222, and 226) of the robotic device (e.g., robotic device 140, robotic device 200). In one scenario, the tracking device 130 may be configured to determine the location of the one or more IR reflectors or emitters prior to beginning operation of the robotic device. In this scenario, the tracking device 130 may provide the location information of the one or more IR reflectors or emitters to a computing device (e.g., processing device 122, computing device 300) for further processing.

In one example, the processing device 122 or computing device 300 may be configured to compare the location information of the one or more IR reflectors or emitters coupled to the robot arm with data stored on a local or remote database that contains information about the robotic device (e.g., a geometric model of the robotic device) to assist in determining a location or position of the robot arm. In one example, the processing device 122 may determine a first position of the robot arm from information provided by the tracking device 130. In this example, the processing device 122 may provide the determined first position of the robot arm to the robotic device or a computing device (e.g., computing device 300). In one example, the robotic device may use the received first position data to perform a calibration of one or more elements (e.g., encoders, actuators) associated with the one or more joints of the robot arm.

In one scenario, an instrument coupled to the robot arm of the robotic device may be used to determine a difference between an expected tip location of the instrument and the actual tip location of the instrument. In this scenario, the robotic device may proceed to move the instrument to a known location by the tracking device 130 so that the tip of the tool is in contact with the known location. The tracking device 130 may capture the location information corresponding to the one or more IR reflectors or emitters coupled to the robot arm and provide that information to the robotic device or a computing device (e.g., processing device 122, computing device 300). Further, either the robotic device or the computing device may be configured to adjust a coordinate system offset between the robotic device and the tracking device 130 based on the expected tip location of the tool and the actual tip location of the tool.

In another aspect, a force or pressure sensor may be coupled to a robot arm (e.g., robot arm 141, links 206, 210, 214, 218, 222, and 226) of a robotic device (e.g., robotic device 140, robotic device 200). In one example, the force or pressure sensor may be located on an end effector of the robot arm. In another example, the force or pressure sensor may be coupled to a given joint of the robotic arm. The force or pressure sensor may be configured to determine when a force or pressure reading is above a resting threshold. The resting threshold may be based on a force or pressure experienced at the sensor when the end effector is holding the instrument without any additional forces or pressure applied to the instrument (e.g., a user attempting to move the instrument). In one example, the robot arm may stop moving if the force or pressure reading is at or below the resting threshold.

In one example, the movement of the robot arm 141 may be controlled by depression of the pedal 142. For example, while the pedal 142 is depressed, the control unit 306 and the movement unit 304 may be configured to receive any measures of force or pressure from the one or more force sensors and used the received information to determine the trajectory of the robot arm 141.

In another example, the movement of the robot arm 141 may be regulated by how much the pedal 142 is depressed. For example, if the user depresses the pedal 142 to the full amount, the robot arm 141 may move with a higher speed compared to when the pedal 142 is depressed at half the amount. In another example, the movement of the robot arm 141 may be controlled by a user interface located on the robotic device.

In one example, the robotic device (e.g., robotic device 140, robotic device 200) may be configured to store, in a local or remote memory, movement data that corresponds to a determined range of movement associated with a surgical tool. In this example, the robotic device may be configured to only travel in one or more directions as defined by the determined range of movement.

In another example, the instrument coupled to the robot arm may include a switch that is in communication with the robotic device. The switch may be in the form of a button that provides a signal to the robotic device to move the robot arm according to the force detected by the force or pressure sensors associated with the end effector or one or more joints of the robot arm. In this example, when the surgeon lets go of the switch, the robotic device will interpret that action as a stopping command and maintain the position of the instrument.

In one example, the surgeon may incorporate the use of a three-dimensional image of the spine and define one or more planes that the instrument should not traverse. In this example, despite force or pressure sensor detecting a force to move the instrument, the robot arm will not allow the surgeon to move the instrument past the defined one or more planes according to the constraints associated with the predefined plan. By way of example, the robotic device may be configured to provide an alert to the surgeon as the instrument approaches the one or more restricted planes.

In another aspect, a robotic device (e.g., robotic device 140, robotic device 200) may be used to navigate one or more surgical instruments and provide the navigation information to a computing device (e.g., processing device 122, computing device 300) for further processing. In one example, the computing device may be configured to determine a virtual representation of the surgical instrument. Further, the computing device may be configured to overlay the virtual representation of the surgical instrument on a two-dimensional or three-dimensional image of the surgical site.

In one example, the robotic device may perform a calibration procedure between the tracking device 130 in order to remove the dependence on the tracking device 130 for location information in the event that a line of sight between the robotic device and the tracking device 130 is blocked. In one example, using a robotic device which has been registered to a navigation system, as described herein, and a patient's three-dimensional image that corresponds to the surgical site may allow the robotic device to become independent of the degradation of accuracy with distance associated with the tracking device 130.

The communication system 308 may include a wired communication interface (e.g., parallel port, USB, etc.) and/or a wireless communication interface (e.g., antenna, transceivers, etc.) to receive and/or provide signals from/to external devices. In some examples, the communication system 308 may receive instructions for operation of the processing device 122. Additionally or alternatively, in some examples, the communication system 308 may provide output data.

The data storage 310 may store program logic 312 that can be accessed and executed by the processor(s) 314. The program logic 312 may contain instructions that provide control to one or more components of the processing device 122, the robotic device 140, the robotic device 200, etc. For example, program logic 312 may provide instructions that adjust the operation of the robotic device 200 based one on or more user defined trajectories associated with a portable instrument. The data storage 310 may comprise one or more volatile and/or one or more non-volatile storage components, such as optical, magnetic, and/or organic storage, and the data storage may be integrated in whole or in part with the processor(s) 314.

The processor(s) 314 may comprise one or more general-purpose processors and/or one or more special-purpose processors. To the extent the processor 314 includes more than one processor, such processors may work separately or in combination. For example, a first processor may be configured to operate the movement unit 304, and a second processor of the processors 314 may operate the control unit 306.

Figure 4:
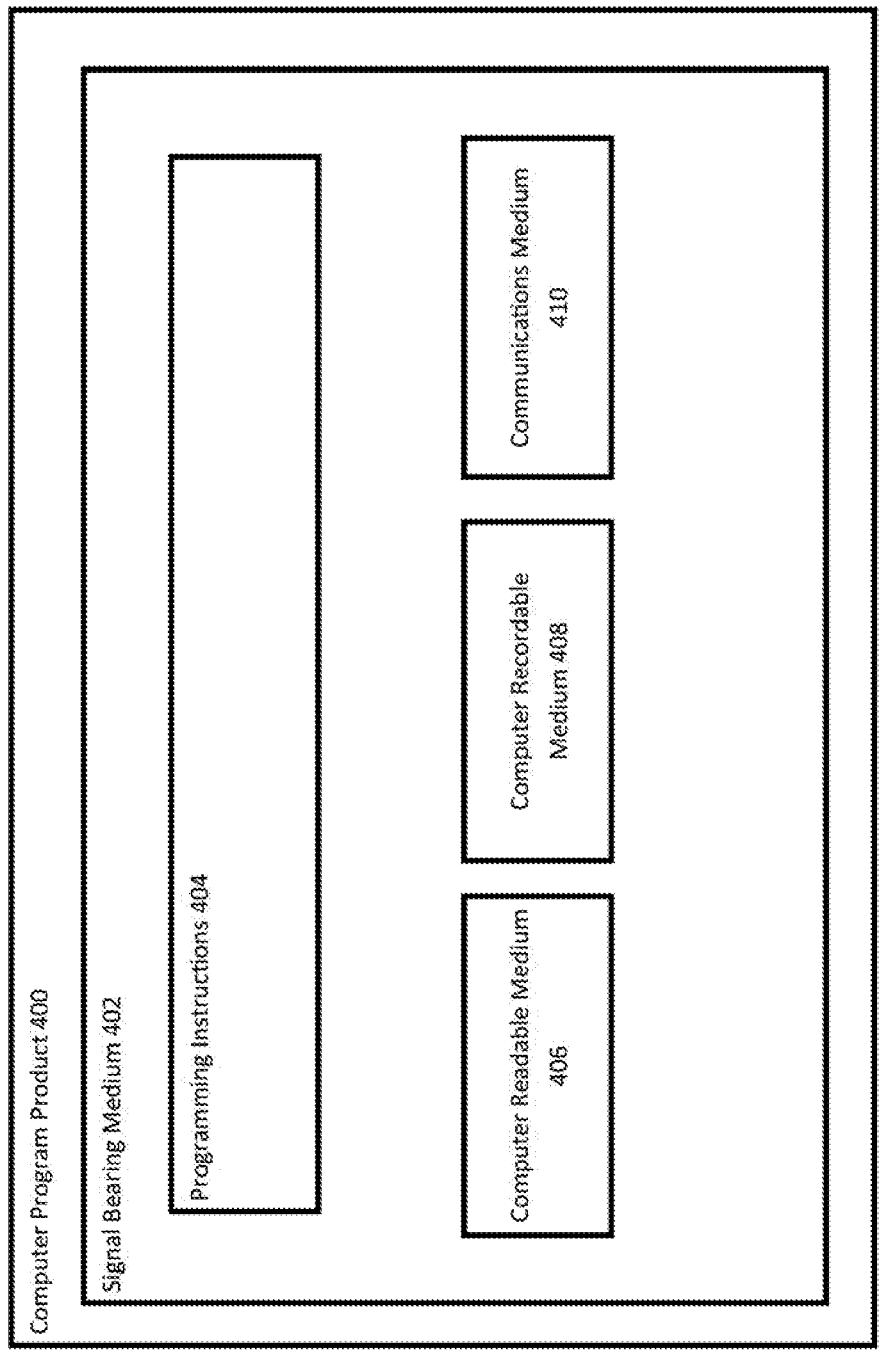
FIG. 4 depicts an example computer readable medium, according to an embodiment of the present disclosure.

FIG. 4 depicts an example computer readable medium configured according to an example embodiment. In example embodiments, an example system may include one or more processors, one or more forms of memory, one or more input devices/interfaces, one or more output devices/interfaces, and machine readable instructions that when executed by the one or more processors cause the system to carry out the various functions tasks, capabilities, etc., described above.

As noted above, in some embodiments, the disclosed techniques (e.g., functions of the robotic device 140, robotic device 200, etc.) may be implemented by computer program instructions encoded on a computer readable storage media in a machine-readable format, or on other media or articles of manufacture. FIG. 4 is a schematic illustrating a conceptual partial view of an example computer program product that includes a computer program for executing a computer process on a computing device, arranged according to at least some embodiments disclosed herein.

In one embodiment, an example computer program product 400 is provided using a signal bearing medium 402. The signal bearing medium 402 may include one or more programming instructions 404 that, when executed by one or more processors may provide functionality or portions of the functionality described above with respect to FIGS. 1-3. In some examples, the signal bearing medium 402 may be a computer-readable medium 406, such as, but not limited to, a hard disk drive, a Compact Disc (CD), a Digital Video Disk (DVD), a digital tape, memory, etc. In some implementations, the signal bearing medium 402 may be a computer recordable medium 408, such as, but not limited to, memory, read/write (R/W) CDs, R/W DVDs, etc. In some implementations, the signal bearing medium 402 may be a communication medium 410 (e.g., a fiber optic cable, a waveguide, a wired communications link, etc.). Thus, for example, the signal bearing medium 402 may be conveyed by a wireless form of the communications medium 410.

The one or more programming instructions 404 may be, for example, computer executable and/or logic implemented instructions. In some examples, a computing device may be configured to provide various operations, functions, or actions in response to the programming instructions 404 conveyed to the computing device by one or more of the computer readable medium 406, the computer recordable medium 408, and/or the communications medium 410.

The computer readable medium 406 may also be distributed among multiple data storage elements, which could be remotely located from each other. The computing device that executes some or all of the stored instructions could be an external computer, or a mobile computing platform, such as a smartphone, tablet device, personal computer, wearable device, etc. Alternatively, the computing device that executes some or all of the stored instructions could be remotely located computer system, such as a server.

Figure 5:
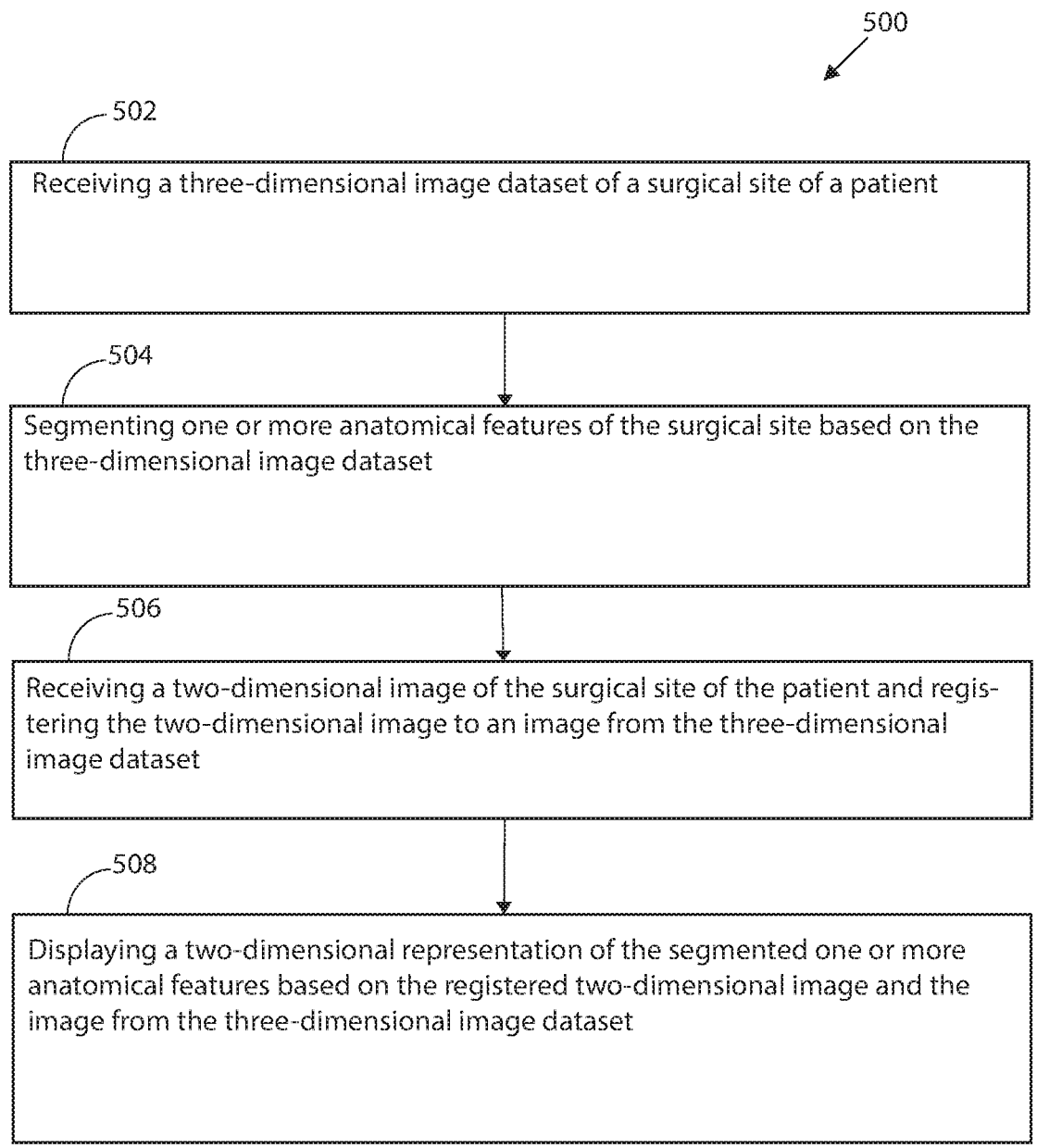
FIG. 5 depicts a flow diagram of an example method, according to an embodiment of the present disclosure.

FIG. 5 is flow diagram of an example method 500, in accordance with at least one embodiment described herein. Although the blocks in FIG. 5 are illustrated in a sequential order, the blocks may in some instances be performed in parallel, and/or in a different order than those described therein. Also, the various blocks may be combined into fewer blocks, divided into additional blocks, and/or removed based upon the desired implementation.

As shown in block 502, the method 500 includes receiving a three-dimensional image dataset of a surgical site of a patient. In one example, the processing device 122 of FIG. 1 may be configured to receive the three-dimensional image dataset based on a three-dimensional scan that is captured via C-Arm 103.

As shown in block 504, the method 500 also includes also includes segmenting one or more anatomical features of the surgical site based on the three-dimensional image dataset. The processing device 122 may include one or more computer executable instructions that are configured to perform a segmentation step on the three-dimensional image dataset of the patient. As used herein, "segmentation" describes a process that identifies individual vertebrae within three-dimensional image data so that the vertebrae can be separated and treated, manipulated, and displayed distinct from one another. The segmentation step may employ a segmentation algorithm that uses imaging processing and image recognition software to automate the spinal level segmentation process. One or more adaptive meshes may be applied to generate a segmented three-dimensional model of the spine. Each vertebra or other anatomical feature can be separately colored to visibly enhance the bone-soft tissue interface, or just the margin can be colored.

Figure 9:
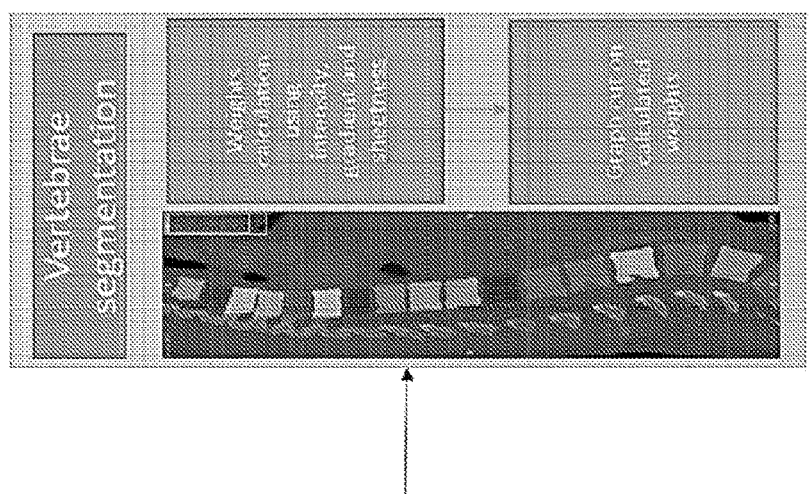
FIG. 9 depicts another exemplary step in a process for segmentation of vertebrae, according to an embodiment of the present disclosure.
Figure 8:
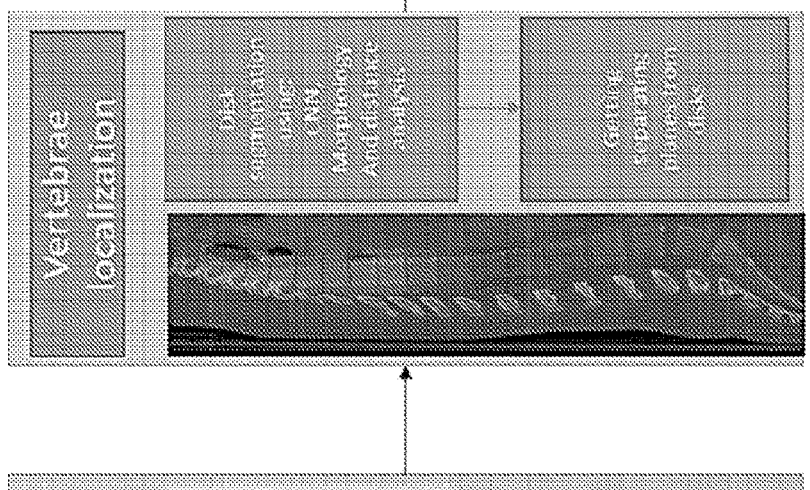
FIG. 8 depicts another exemplary step in a process for segmentation of vertebrae, according to an embodiment of the present disclosure.
Figure 7:
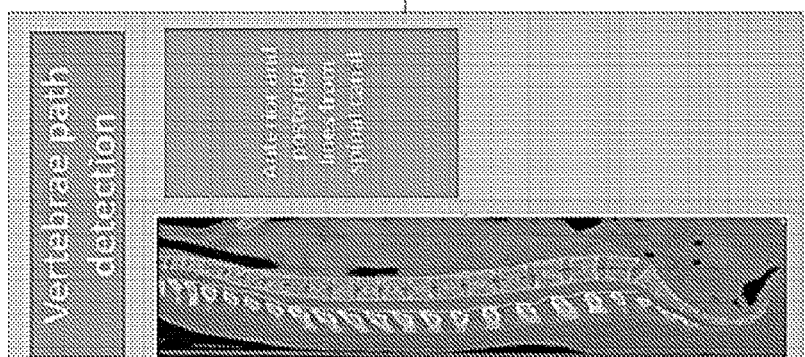
FIG. 7 depicts another exemplary step in a process for segmentation of vertebrae, according to an embodiment of the present disclosure.
Figure 6:
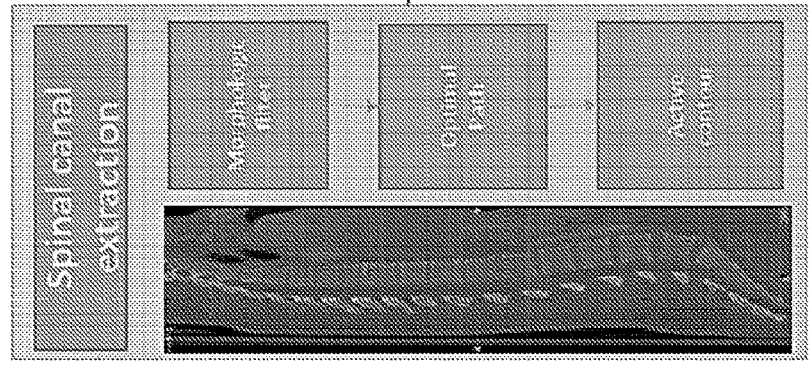
FIG. 6 depicts an exemplary step in a process for segmentation of vertebrae, according to an embodiment of the present disclosure.

FIGS. 6-9 illustrate an exemplary process for segmentation of vertebrae. In one example, the segmentation of the vertebrae can be automatic, and can include one or more of spinal canal extraction, vertebrae path detection, vertebrae localization, and vertebrae segmentation. For spinal canal extraction, as shown in FIG. 6, preprocessing of the canal may be performed in the axial plane, and the morphology of the canal in each axial slice of the three-dimensional volume can be reconstructed and connected to complete the canal segmentation. In one example, the extraction process includes the use of an active contour model. As shown in FIG. 7, based on the spinal canal segmentation, the posterior line and anterior lines of the vertebrae defined by the canal can be determined. As shown in FIG. 8, the vertebrae can be localized by first detecting vertebral discs using a convolutional neural network algorithm and/or morphology information of the discs. Secondly, distance analysis can be used to find missing discs or identify false detection. Based on the disc surfaces identified, the separating planes between adjacent vertebrae can be determined. As shown in FIG. 9, the vertebrae are separated from surrounding tissue (e.g., canal and discs) and weighting can be added based on image intensity, intensity gradient, and sheetness of the three-dimensional dataset to refine vertebrae segmentation.

In some embodiments, the segmentation is for one vertebra, more than one vertebrae, or even each vertebra of the entire spinal cord. After segmentation, single vertebra three-dimensional datasets can be generated for each vertebra that has been segmented. In some embodiments, the single vertebra three-dimensional image dataset is created by cutting the relevant vertebra out based on the segmentation. In some embodiments, the single vertebra three-dimensional image dataset is generated using smoothening. For example, the 2D manifold that connects the edge of the segmented vertebra and other parts of the 3D data is smoothed out using Poisson blending. Two or more single vertebra three-dimensional image datasets can be combined into a single dataset containing two or more vertebrae. The combination can include a unique transformation for each single vertebrae three-dimensional image dataset. The transformation can include three-dimensional translation and/or three-dimensional rotation relative to one dataset being combined or a reference coordinate system. In some embodiments, one or more sub-steps in segmentation may implement a Deep Neural Network (DNN) trained to estimate the boundary of vertebrae in three-dimensional volumes, based on shape and voxel intensity. For example, the three-dimensional scan may be split into patches and a neural network may be used to segment each patch.

Referring back to FIG. 5, as shown in block 506, the method 500 also includes receiving a two-dimensional image of the surgical site of the patient and registering the two-dimensional image to an image from the three-dimensional image dataset. In one example, the processing device 122 of FIG. 1 may be configured to receive the two-dimensional image based on a scan that is captured via the C-Arm 103. In some embodiments, registration includes repetitively generating Digitally Reconstructed Radiographs (DRRs) and evaluating each DRR using a predetermined cost function until the cost function is optimized thereby indicating an optimal match of the DRR to the two-dimensional image. The optimal DRR then can be used for further processing.

In some embodiments, registration includes one or more sub-modules that can be used in combination. For example, one submodule can use the outputs of one or more other sub-modules as its inputs. In one example, one submodule, 6 DOF, can be configured to create a six degrees of freedom parameter space in which pseudo quaternion (3 parameters) representation can be used for rotation. In some embodiments, the 6 DOF submodule can calculate the three-dimensional coordinates and orientation of the DRR (e.g., x, y, z, yaw, pitch, and roll). The 6 DOF submodule can be configured to generate the back and/or forth transformations between registration matrixes and compact six degrees of freedom parameters space.

One submodule, DRR generation module, can be used to repetitively generatie DRRs based on the initial starting point (in the first iteration during optimization), or based on the previous DRRs and/or the previous value(s) of the cost function in later iterations during optimization. In some embodiments, the DRR generation module includes one or more inputs selected from: the original three-dimensional image dataset, e.g., the preoperative CT scan, the segmented three-dimensional image dataset, the single vertebra three-dimensional image dataset, parameters of the image capturing device (e.g., C-Arm 103) such as position and orientation, parameter of the image such as image size, center point, and pixel size.

In some examples, the DRR generated herein is equivalent to rotating and/or translating the segmented three-dimensional image dataset relative to an image capturing device, e.g., X-ray source and X-ray detector, and acquiring two-dimensional images based on the relative position thereof. The relative rotation and/or translation between the three-dimensional image dataset and the device can determine what is included in the DRR.

One submodule can be configured to find a cost function that its extremum (e.g., a local minimum) may reflect the best or optimal alignment between the DRR's images and the two-dimensional images. As an example, spatial gradient correlation between the DRR and the two-dimensional images can be calculated and then the value of the cost function can be represented by a single score of the input parameters (e.g., x, y, z, yaw, pitch, and roll).

One submodule can be configured to perform coarse optimization of the cost function, optionally after an initial starting point has been determined by a user or automatically selected by a software module. The coarse optimization module herein can use a covariance matrix adaptation evolution strategy (CMAES) optimization process which is a non-deterministic optimization process to optimize the cost function. The advantage can be that coarse optimization can avoid local minima, and cover large search area. In some embodiments, optimization process other than CMAES can be used for coarse optimization.

One submodule can be configured to perform fine-tuning optimization of the cost function, optionally after a coarse optimization has been performed. The fine-tuning optimization module can use gradient descent optimization process, a deterministic process, to optimize process that optimize the cost function. One advantage of the fine-tuning optimization can be that it is accurate and can find the best location for optimization, but it cannot differ between global and local minima.

In some embodiments, the registration herein includes an optimization module that may use one or more optimization algorithms such as CMAES and gradient descent optimization. In some embodiments, the optimization module includes a coarse optimization module and a fine-tuning module. In some embodiments, optimization module used herein are not limited to CMAES and gradient descent optimization processes.

In some embodiments, a user is asked to provide an input using an input device to provide information related to the vertebrae to be registered. In one example, the user can directly click on the vertebra that needs registration with a dot in an undistorted two-dimensional image either in a single view or using multiple views. Registering only the vertebrae of interest may be advantageously save time and allow faster update of the three-dimensional image dataset.

In some embodiments, a number of three-dimensional image data files, each containing a single vertebra, may be provided for registration. Other information such as vertebra center, body to spinous process direction, and/or upper end plate direction of each vertebra may also be provided to facilitate registration. Such information can be automatically obtained in the segmentation process disclosed herein and then automatically input to a registration module or another step. Other inputs to the registration process or steps may include undistorted two-dimensional images including calibration matrix, internal matrix, and/or external matrix. The user input on the location of the vertebra on the two-dimensional image or undistorted images can also be provided.

In some embodiments, the DRR may be output for updating the pre-operative three-dimensional image dataset. In some embodiments, the registration matrix which includes translation and rotation (e.g., yaw, pitch, roll) for each vertebra is output so that the user can later combine the vertebrae each modified by the registration matrix. The registration matrix herein is a transformation matrix that provides three-dimensional rigid transformation of vertebrae or otherwise anatomical features of interest.

As shown in block 508, the method 500 also includes displaying a two-dimensional representation of segmented one or more anatomical features based on the registered two-dimensional image and the image from the three-dimensional image dataset. In one example, the two-dimensional representation of the segmented one or more anatomical features includes a two-dimensional representation of a single vertebra. In another example, the two-dimensional representation of the segmented one or more anatomical features includes a two-dimensional representation of a plurality of vertebrae.

Figure 10:
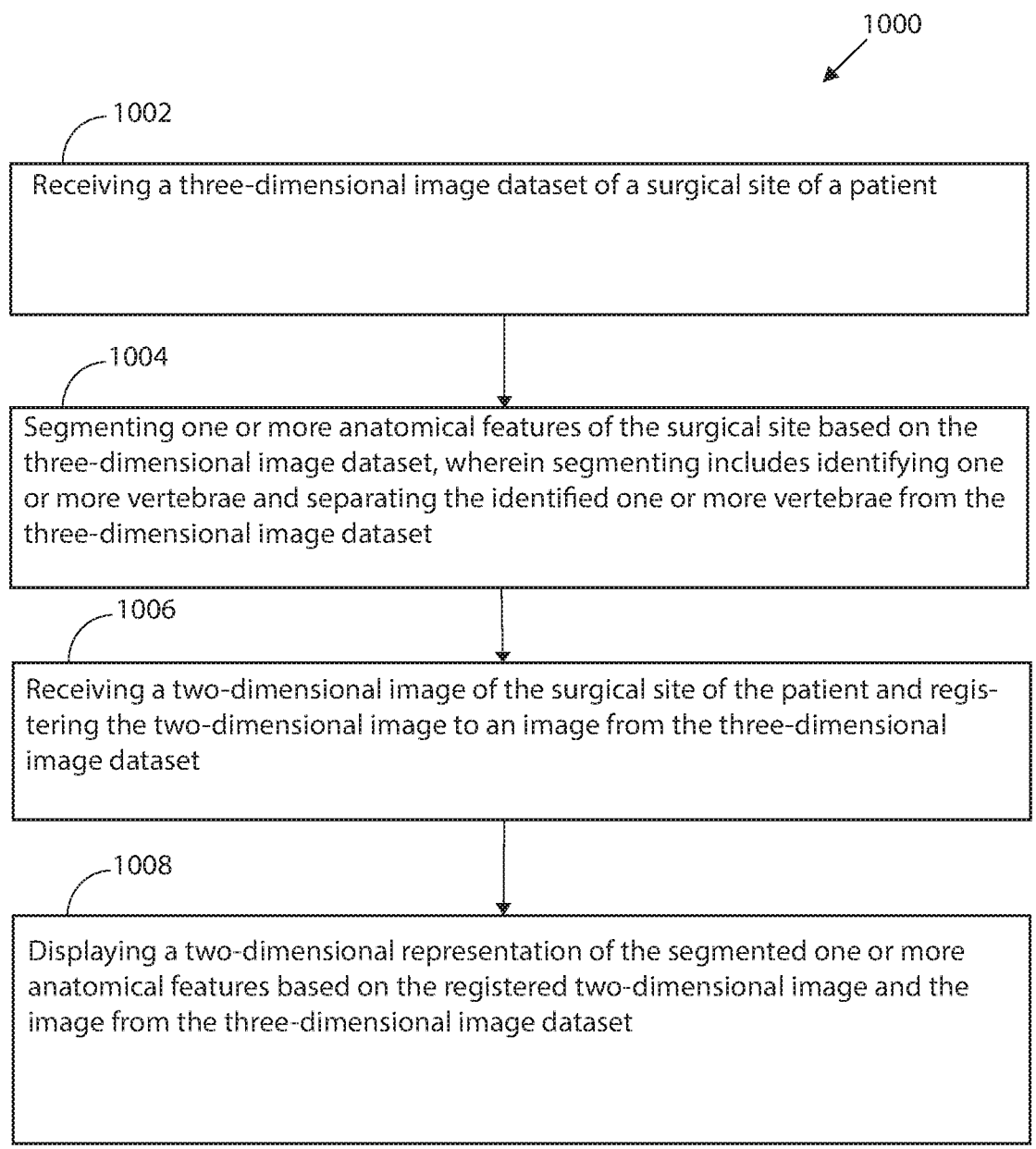
FIG. 10 depicts a flow diagram of another example method, according to an embodiment of the present disclosure.

FIG. 10 is flow diagram of an example method 1000, in accordance with at least one embodiment described herein. Although the blocks in FIG. 10 are illustrated in a sequential order, the blocks may in some instances be performed in parallel, and/or in a different order than those described therein. Also, the various blocks may be combined into fewer blocks, divided into additional blocks, and/or removed based upon the desired implementation.

As shown by block 1002, the method 1000 includes receiving a three-dimensional image dataset of a surgical site of a patient. In one example, the processing device 122 of FIG. 1 may be configured to receive the three-dimensional image dataset based on a three-dimensional scan that is captured via C-Arm 103.

As shown by block 1004, the method 1000 also includes segmenting one or more anatomical features of the surgical site based on the three-dimensional image dataset, wherein segmenting includes identifying one or more vertebrae and separating the identified one or more vertebrae from the three-dimensional image dataset. In one example, the surgical site includes at least a portion of the spine of the patient and segmenting the one or more anatomical features of the surgical site based on the three-dimensional image dataset includes identifying one or more spinals levels within the three-dimensional image dataset.

As shown by block 1006, the method 1000 also includes receiving a two-dimensional image of the surgical site of the patient and registering the two-dimensional image to an image from the three-dimensional image dataset. In one example, registering the two-dimensional image to an image from the three-dimensional image dataset the method includes generating one or more three-dimensional image datasets corresponding to the separated identified one or more vertebrae. Continuing with this example, the method 1000 includes registering the two-dimensional image to an image from the generated one or more three-dimensional image datasets.

In another example, registering the two-dimensional image to an image from the three-dimensional image dataset the method includes generating one or more three-dimensional image datasets corresponding to the separated identified one or more vertebrae and combining two or more three-dimensional image datasets from the generated one or more three-dimensional image datasets. Continuing with this example, the method 1000 includes registering the two-dimensional image to an image from the combined two or more three-dimensional image datasets. In one example, the one or more anatomical features includes one or more vertebrae and registering the two-dimensional image to an image from the three-dimensional image dataset the method includes receiving a user input corresponding to information related to the one or more vertebrae.

As shown by block 1008, the method 1000 also includes displaying a two-dimensional representation of the segmented one or more anatomical features based on the registered two-dimensional image and the image from the three-dimensional image dataset. In one example, displaying the two-dimensional representation of the segmented one or more anatomical features based on the registered two-dimensional image and the image from the three-dimensional image dataset includes displaying a plurality of two-dimensional representations of a single vertebra. In another example, displaying the two-dimensional representation of the segmented one or more anatomical features based on the registered two-dimensional image and the image from the three-dimensional image dataset includes displaying a plurality of two-dimensional representations of a plurality of vertebrae.

Figure 11:
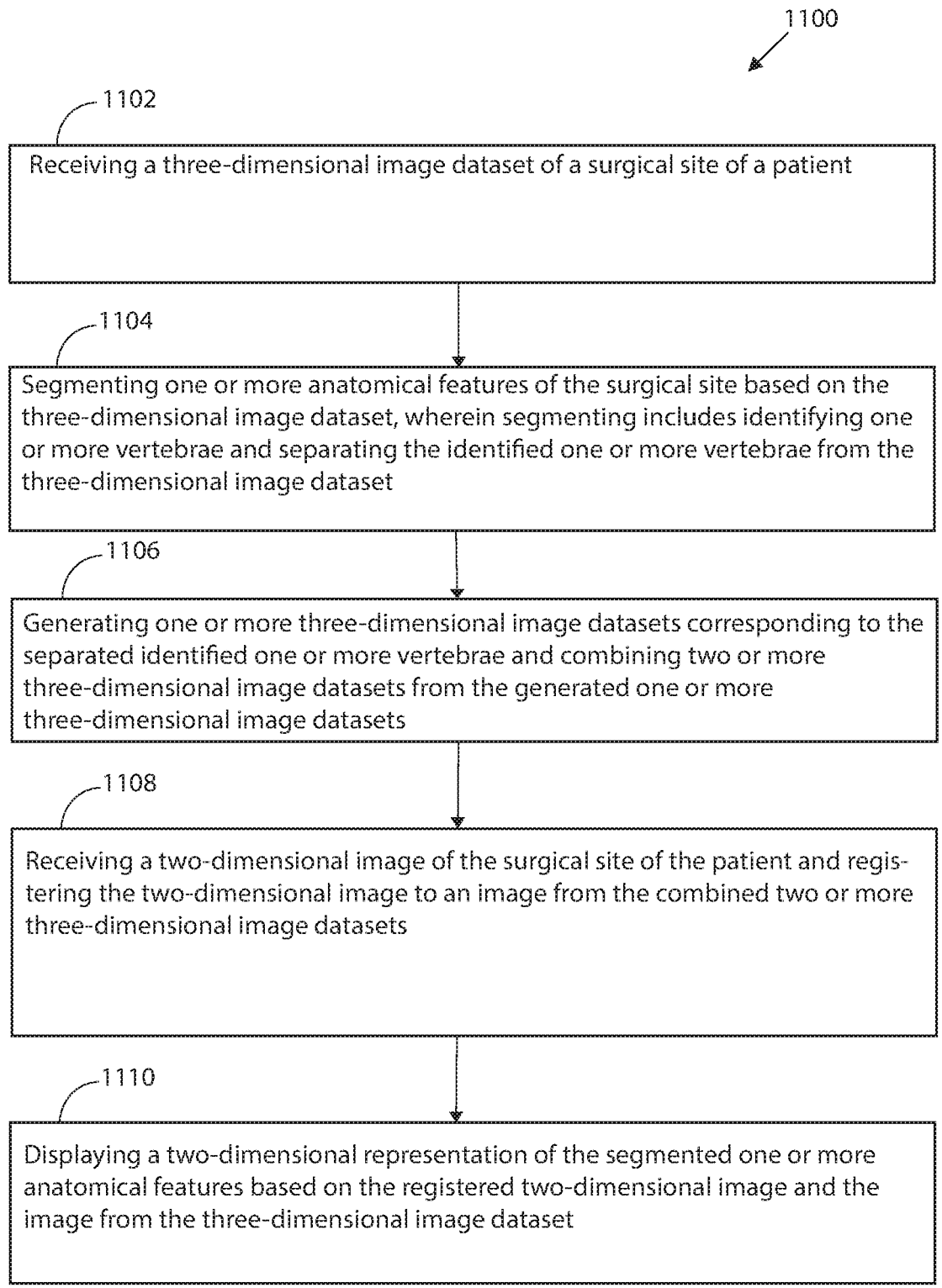
FIG. 11 depicts a flow diagram of another example method, according to an embodiment of the present disclosure.

FIG. 11 is flow diagram of an example method 1100, in accordance with at least one embodiment described herein. Although the blocks in FIG. 11 are illustrated in a sequential order, the blocks may in some instances be performed in parallel, and/or in a different order than those described therein. Also, the various blocks may be combined into fewer blocks, divided into additional blocks, and/or removed based upon the desired implementation.

As shown by block 1102, the method 1100 includes receiving a three-dimensional image dataset of a surgical site of a patient. In one example, the processing device 122 of FIG. 1 may be configured to receive the three-dimensional image dataset based on a three-dimensional scan that is captured via C-Arm 103.

As shown by block 1104, the method 1100 also includes segmenting one or more anatomical features of the surgical site based on the three-dimensional image dataset, wherein segmenting includes identifying one or more vertebrae and separating the identified one or more vertebrae from the three-dimensional image. In one example, the surgical site includes at least a portion of the spine of the patient and segmenting the one or more anatomical features of the surgical site based on the three-dimensional image dataset includes identifying one or more spinals levels within the three-dimensional image dataset.

As shown by block 1106, the method 1100 also includes generating one or more three-dimensional image datasets corresponding to the separated identified one or more vertebrae and combining two or more three-dimensional image datasets from the generated one or more three-dimensional image datasets.

As shown by block 1108, the method 1100 also includes receiving a two-dimensional image of the surgical site of the patient and registering the two-dimensional image to an image from the combined two or more three-dimensional image datasets. In one example, the one or more anatomical features includes one or more vertebrae and registering the two-dimensional image to an image from the three-dimensional image dataset the method includes receiving a user input corresponding to information related to the one or more vertebrae.

As shown by block 1110, the method 1100 also includes displaying a two-dimensional representation of the segmented one or more anatomical features based on the registered two-dimensional image and the image from the three-dimensional image dataset. In one example, displaying the two-dimensional representation of the segmented one or more anatomical features based on the registered two-dimensional image and the image from the three-dimensional image dataset includes displaying a plurality of two-dimensional representations of a single vertebra. In another example, displaying the two-dimensional representation of the segmented one or more anatomical features based on the registered two-dimensional image and the image from the three-dimensional image dataset includes displaying a plurality of two-dimensional representations of a plurality of vertebrae.

The flow diagrams of FIGS. 5, 10, and 11 show the functionality and operation of possible implementations of the present embodiment. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer-readable media that stores data for short periods of time, such as register memory, processor cache, or Random Access Memory (RAM), and/or persistent long term storage, such as read only memory (ROM), optical or magnetic disks, or compact-disc read only memory (CD-ROM), for example. The computer readable media may be able, or include, any other volatile or non-volatile storage systems. The computer readable medium may be considered a computer readable storage medium, a tangible storage device, or other article of manufacture, for example.

Alternatively, each block in FIGS. 5, 10, and 11 may represent circuitry that is wired to perform the specific logical functions in the process. An illustrative method, such as the one shown in FIGS. 5, 10, and 11 may be carried out in whole in or in part by a component or components in the cloud. However, it should be understood that the example methods may instead be carried out by other entities or combinations of entities (i.e., by other computing devices and/or combination of computer devices), without departing from the scope of the invention. For example, functions of the method of FIGS. 5, 10, and 11 may be fully performed by a computing device (or components of a computing device such as one or more processors), or may be distributed across multiple components of the computing device, across multiple computing devices, and/or across a server.

While the inventive features described herein have been described in terms of a preferred embodiment for achieving the objectives, it will be appreciated by those skilled in the art that variations may be accomplished in view of those teachings without deviating from the spirit or scope of the invention.

What is claimed is:

1. A method comprising:
   receiving a three-dimensional image dataset of a surgical site of a patient;
   segmenting one or more anatomical features of the surgical site based on the three-dimensional image dataset;
   receiving a two-dimensional image of the surgical site of the patient and registering the two-dimensional image to an image from the three-dimensional image dataset; and
   displaying a two-dimensional representation of the segmented one or more anatomical features based on the registered two-dimensional image and the image from the three-dimensional image dataset,
   wherein the segmenting is automatic spinal canal extraction and includes preprocessing of a spinal canal in an axial plane and determining a morphology of the spinal canal in each axial slice of the three-dimensional image dataset.

2. The method of claim 1, segmenting the one or more anatomical features of the surgical site based on the three-dimensional image dataset includes identifying one or more vertebrae and separating the identified one or more vertebrae from the three-dimensional image dataset.

3. The method of claim 2, wherein registering the two-dimensional image to an image from the three-dimensional image dataset the method includes:
   generating one or more three-dimensional image datasets corresponding to the separated identified one or more vertebrae; and
   registering the two-dimensional image to an image from the generated one or more three-dimensional image datasets.

4. The method of claim 3, wherein registering the two-dimensional image to an image from the three-dimensional image dataset the method includes:
   generating one or more three-dimensional image datasets corresponding to the separated identified one or more vertebrae;
   combining two or more three-dimensional image datasets from the generated one or more three-dimensional image datasets; and
   registering the two-dimensional image to an image from the combined two or more three-dimensional image datasets.

5. The method of claim 1, wherein displaying the two-dimensional representation of the segmented one or more anatomical features based on the registered two-dimensional image and the image from the three-dimensional image dataset includes:
   displaying a plurality of two-dimensional representations of a single vertebra.

6. The method of claim 1, wherein displaying the two-dimensional representation of the segmented one or more anatomical features based on the registered two-dimensional image and the image from the three-dimensional image dataset includes:
   displaying a plurality of two-dimensional representations of a plurality of vertebrae.

7. The method of claim 1, wherein the one or more anatomical features includes one or more vertebrae, wherein registering the two-dimensional image to an image from the three-dimensional image dataset the method includes:
   receiving a user input corresponding to information related to the one or more vertebrae.

8. The method of claim 1, wherein the surgical site includes at least a portion of the spine of the patient, segmenting the one or more anatomical features of the surgical site based on the three-dimensional image dataset includes identifying one or more spinals levels within the three-dimensional image dataset.

* * * * *